United States Patent
Seemeyer et al.

(10) Patent No.: US 11,117,854 B2
(45) Date of Patent: Sep. 14, 2021

(54) ESTER COMPOUNDS, METHOD FOR THE PREPARATION THEREOF AND USE THEREOF

(71) Applicant: Kübler Lubrication München SE & Co. KG, Munich (DE)

(72) Inventors: Stefan Seemeyer, Munich (DE); Maximilian Erhard, Munich (DE); Thomas Kilthau, Munich (DE); Ling Ma, Munich (DE)

(73) Assignee: KLÜBER LUBRICATION MÜNCHEN SE & CO. KG, Munich (DE)

( * ) Notice: Subject to any disclaimer, the term of this patent is extended or adjusted under 35 U.S.C. 154(b) by 28 days.

(21) Appl. No.: 16/492,751

(22) PCT Filed: Mar. 26, 2018

(86) PCT No.: PCT/EP2018/000117
§ 371 (c)(1),
(2) Date: Sep. 10, 2019

(87) PCT Pub. No.: WO2018/177588
PCT Pub. Date: Oct. 4, 2018

(65) Prior Publication Data
US 2020/0071256 A1    Mar. 5, 2020

(30) Foreign Application Priority Data

Mar. 29, 2017  (DE) .................... 10 2017 003 040.5
Mar. 14, 2018  (DE) .................... 10 2018 002 041.0

(51) Int. Cl.
*C07C 69/608*  (2006.01)
*C07C 67/05*  (2006.01)
(Continued)

(52) U.S. Cl.
CPC ............ *C07C 69/608* (2013.01); *C07C 67/05* (2013.01); *C07C 67/08* (2013.01); *C10M 105/42* (2013.01);
(Continued)

(58) Field of Classification Search
None
See application file for complete search history.

(56) References Cited

U.S. PATENT DOCUMENTS

2012/0322707 A1 * 12/2012 Bredsguard .......... C10M 129/10
                                                        508/465
2013/0261325 A1    10/2013 Forest et al.
2016/0108343 A1     4/2016 Jeon et al.

FOREIGN PATENT DOCUMENTS

WO    2012173666 A1    12/2012
WO    2014078149 A1     5/2014

OTHER PUBLICATIONS

International Search Report corresponding to international application No. PCT/EP2018/000117 dated Jul. 25, 2018 ( 14 pages).
(Continued)

*Primary Examiner* — Vishal V Vasisth
(74) *Attorney, Agent, or Firm* — Maginot, Moore & Beck, LLP

(57) ABSTRACT

Ester compounds, such as for use in a lubricant, are based on di-, tri- or higher functional carboxylic acids according to formula (I).

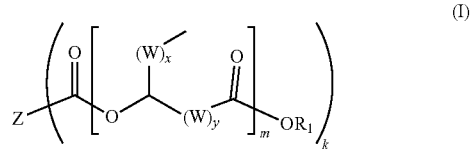

15 Claims, 2 Drawing Sheets

(51) Int. Cl.
*C07C 67/08* (2006.01)
*C10M 105/42* (2006.01)
*C10N 20/02* (2006.01)
*C10N 20/00* (2006.01)
*C10N 30/02* (2006.01)
*C10N 40/02* (2006.01)
*C10N 40/04* (2006.01)
*C10N 40/00* (2006.01)

(52) U.S. Cl.
CPC ... *C07C 2601/16* (2017.05); *C10M 2207/301* (2013.01); *C10N 2020/02* (2013.01); *C10N 2020/081* (2020.05); *C10N 2030/02* (2013.01); *C10N 2040/02* (2013.01); *C10N 2040/04* (2013.01); *C10N 2040/38* (2020.05)

(56) References Cited

OTHER PUBLICATIONS

Arukali Sammaiah et al, "Synthesis and physical properties of novel estolides from dicarboxylic acids and methyl ricinoleate: Synthesis and physical properties of novel estolides," European Journal of Lipid Science and Technology, vol. 118, No. 3, Mar. 1, 2016 pp. 486-494.

Xu Xu et al., "Enhanced thermal and mechanical properties of lignin/polypropylene wood-plastic composite by using flexible segment-containing reactive compatibilizer," Macromolecular Research, vol. 22, No. 10, Sep. 24, 2014, pp. 1048-1089.

Gorla Geethanjali et al., "Synthesis, Characterization, and Evaluation of Castor Oil-Based Acylated Derivatives as Potential Lubricant Base Stocks," Industrial & Engineering Chemistry Research, vol. 55, No. 34, Aug. 22, 2016, pp. 9109-9117.

* cited by examiner

Polyvalent carboxylic acid:

Dimer acid (S1) 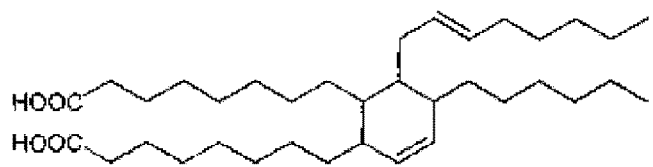

hyd. dimer acid (S2) 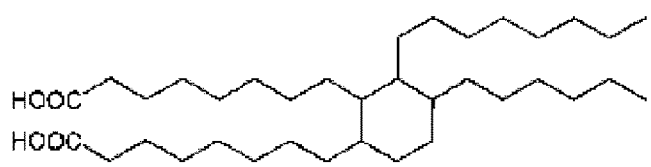

Trimer acid (S3, structure too complex)

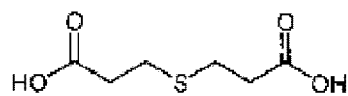
3,3'-Thiodipropionic acid (S4)

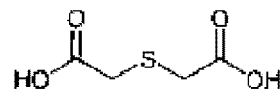
2,2'-thiodiacetic acid (S5)

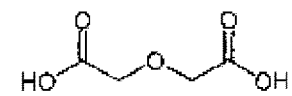
Diglycolic acid (S6)

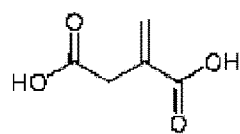
Itaconic acid (S7)

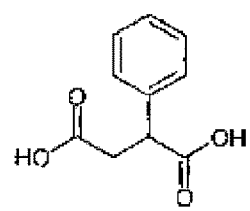
Phenylsuccinic acid (S8)

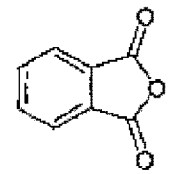
Phthalic anhydride (S9)

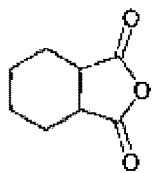
Cyclohexane-1,2-dicarboxylic anhydride (S10)

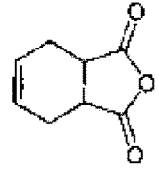
Cyclohexene-4,5-dicarboxylic anhydride (S11)

Figure 1: Structure of the polyvalent carboxylic acids $Z(COOH)_{2/3}$

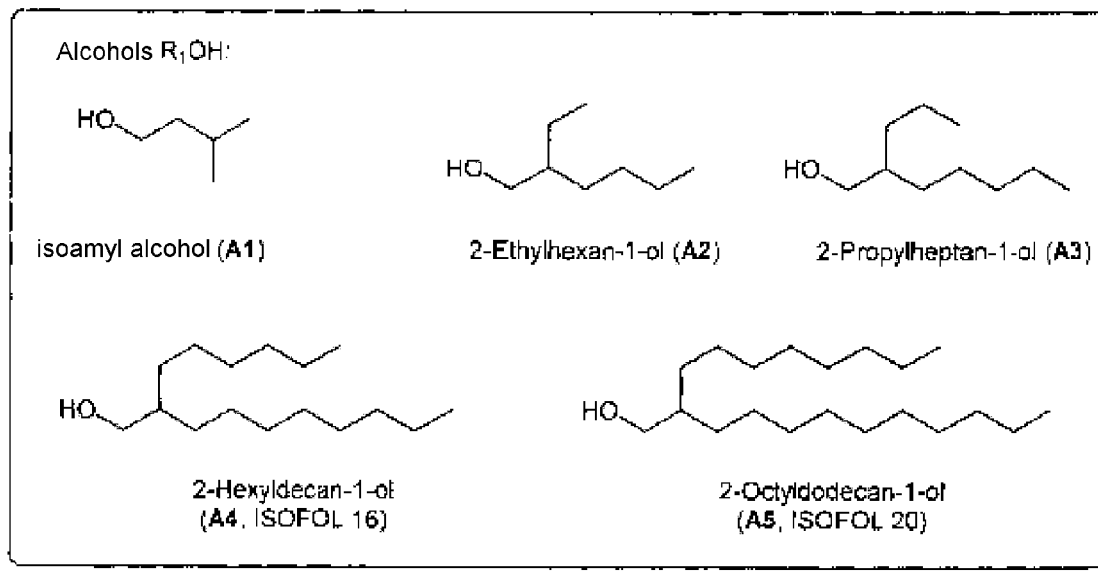
Figure 2: Structure of the alcohols $R_1OH$
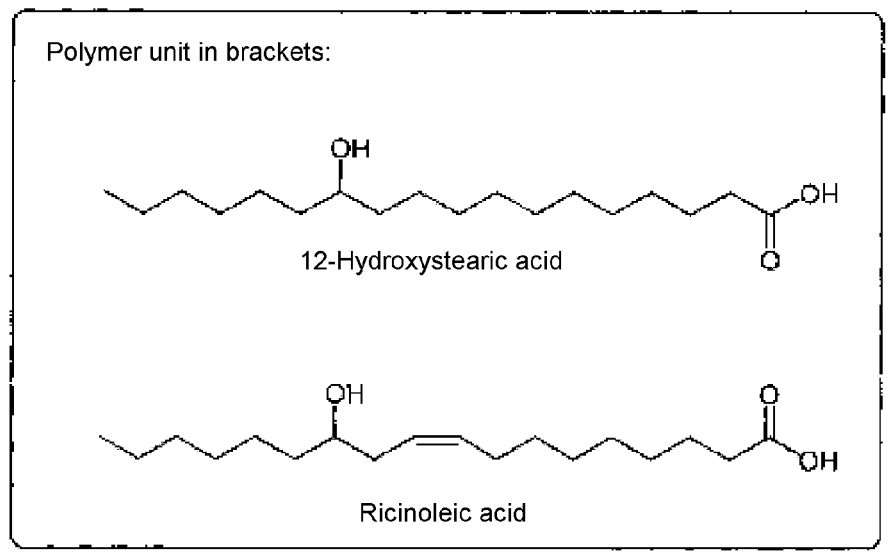
Figure 3: Structure of the polymer units 12-HSA and ricinoleic acid

ESTER COMPOUNDS, METHOD FOR THE PREPARATION THEREOF AND USE THEREOF

This application is a 35 U.S.C 371 National Stage application of PCT/EP2018/000117, filed Mar. 26, 2018 and claiming priority to German Application Nos. DE 10 2017 003 040.5, filed on Mar. 29, 2017, DE 10 2018 002 041.0, filed on Mar. 14, 2018. The entire contents of the above-mentioned patent applications are incorporated herein by reference as part of the disclosure of this U.S. application.

BACKGROUND

The invention relates to novel ester compounds based on di-, tri- or higher functional carboxylic acids according to the general formula (I),

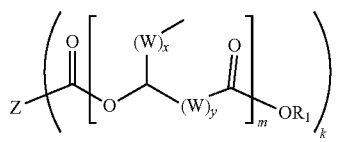

methods for the preparation thereof and use thereof in lubricants.

Ester compounds have been used ever more frequently in lubricant formulations in the last few years. In the case of the known ester compounds, when the lubricant is used in the presence of water, the ester is cleaved to the fatty acid and the alcohol. This reaction can be catalyzed, for example, by acids or bases or by copper. This results in the destruction of the molecules. Thus, the lubricants lose their lubricating effect. Therefore, there is a high demand for esters stable to hydrolysis.

Furthermore, conventional lubricants are unsuitable, for example, for high-temperature applications since they can be destroyed at high temperatures by oxidation and/or thermal decomposition processes and by polymerization, and hence their lubricating properties and effects are greatly restricted. In decomposition reactions, the lubricant is cleaved to give volatile components of low molecular weight. The zo evaporation of these volatile components leads to unwanted changes in viscosity, loss of oil, and to excess vapor formation. This likewise results in a loss of lubricity. The polymerization also causes the lubricants to lose their lubricity owing to the formation of insoluble polymerization products. This soiling has to be removed, which increases maintenance operations. Furthermore, chemical wastes are produced, which have to be disposed of in a complex manner. Owing to the increased cleaning and maintenance work, there is an increase in the shutdown times of the devices to be lubricated. Overall, the use of unsuitable lubricants in high-temperature applications leads to higher costs since the machinery is soiled and there is a high demand for lubricants. Furthermore, there is a drop in product quality.

In order to meet the various demands, lubricants must have, among other qualities, high stability, low coefficients of friction and high wear resistances. High temperatures often occur in the case of use in chains, ball bearings and slide bearings, in motor vehicle technology, in conveying technology, in mechanical engineering, in office technology and industrial plants and machinery, but also in the fields of domestic appliances and consumer electronics.

High processing temperatures often occur in food processing, as in the case of cooking, baking, boiling, roasting, braising, sterilizing, frying and steaming. Various equipment is used in these operations. Lubrication of this equipment requires high-temperature-resistant lubricants.

Particular demands are made on the base oils for lubricating equipment for the processing of foods in relation to environmental compatibility and toxicity. In principle, a food-compatible lubricant H1 should be suitable when the lubricant can come into zo indirect or direct contact with foods, semi-luxury goods and foodstuffs. The preferred fields of use in the food industry include chains in baking ovens and other high-temperature applications, and also transport gears, especially trolleys and bearings thereof.

These lubricants are subject to legal requirements, such as certification under NSF/H1 or NSF/H2.

In the case of applications of lubricants in the marine sector that are usually below the waterline, there is the risk of contamination of the marine or water environment as a result of the escape of lubricants. Even though attempts are made to seal the water side as best possible in these applications, lubricant losses are an everyday occurrence. According to a source at the United States Environmental Protection Agency in 2011, different ship constructions lose from less than one liter of lubricant up to 20 liters per day per ship.

However, the lubricants known to date are unable to meet all these requirements.

Esters comprising higher functional carboxylic acids as the central molecule are known, for example dimer acid. These compounds, however, are generally non-biodegradable. An advantage of these compounds is their excellent technical properties. Furthermore, preparation of esters from oleic acid oligomers and/or 12-hydroxystearic acid oligomers is known. These substances are biodegradable, stable to hydrolysis and can be produced from renewable raw materials.

SUMMARY OF THE INVENTION

One object of the present invention, therefore, is to provide novel ester compounds which satisfy the requirements specified above, i.e. they must be usable in lubricants and able to be prepared from simple and readily accessible starting materials. Moreover, a synthetic method for preparing these ester compounds should be provided with which a high yield and high selectivity are achieved and simple purification is possible.

This object is achieved by the provision of novel methods for preparing ester compounds.

The ester compound according to the invention has the following specific general formula (I):

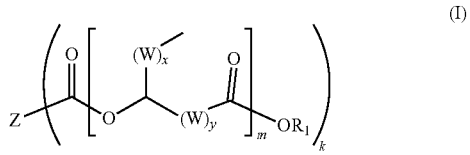

in which:

the radical Z is selected from the structural element of a carboxylic acid without carboxyl units, which comprise at least one sp3-hybridized carbon atom with one or no hydrogen atom, or at least one sp2-hybridized carbon atom without hydrogen atoms, or at least one heteroatom in the chain/ring or as substituent, especially hydrogenated or non-hydrogenated dimer acids, hydrogenated or non-hydrogenated trimer acids, terephthalic acid, isophthalic acid, phthalic acid, trimellitic acid, hemimellitic acid, zo trimesic acid, citric acid, itaconic acid, oxalic acid, 2,2'-thiodiacetic acid, 3,3'-thiodipropionic acid, admergic acid, 2,5-furandicarboxylic acid, cyclohexane-1,4-dicarboxylic acid, cyclohexane-1,2-dicarboxylic acid, phenylsuccinic acid, glutamic acid, aspartic acid, ethylenediaminetetraacetic acid, diethylenetriaminepentaacetic acid, propylenediaminetetraacetic acid, nitrilotriacetic acid, diglycolic acid and iminodiacetic acid, the radical $R^1$ is selected from the group consisting of hydrogen, branched or unbranched $C_1$- to $C_{30}$-alkyl radicals, branched or unbranched $C_1$- to $C_{30}$-alkenyl radicals, $C_7$- to $C_{30}$-arylalkyl radicals and/or $C_1$- to $C_{30}$-heteroarylalkyl radicals and $C_4$- to $C_{30}$-aryl radicals, the radical W is selected from the group consisting of —$CH_2$— and/or —CH=CH—, x is an integer from 1 to 20, preferably 1 to 10,
y is an integer from 1 to 20, preferably 1 to 10,
m is an integer from 1 to 10, preferably 1 to 5,
k is an integer from 2 to 10, preferably 2 to 5.

As radical Z, particular preference is given to using polyvalent carboxylic acids selected from the group consisting of hydrogenated or non-hydrogenated dimer acid, hydrogenated or non-hydrogenated trimer acid, phthalic acid, itaconic acid, oxalic acid, 2,2'- thiodiacetic acid, 3,3'-thiodipropionic acid, admergic acid, 2,5-furandicarboxylic acid, cyclohexane-1,4-dicarboxylic acid, cyclohexane-1,2-dicarboxylic acid, phenylsuccinic acid, diglycolic acid.

A preferred ester compound according to the invention has the following specific general formula (II):

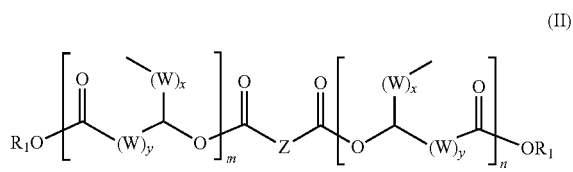

in which
the radical Z is selected from the structural element of a carboxylic acid without carboxyl units, which comprise at least one sp3-hybridized carbon atom with one or no hydrogen atom, or at least one sp2-hybridized carbon atom without hydrogen atoms, or at least one heteroatom in the chain/ring or as substituent, especially hydrogenated or non-hydrogenated dimer acids, terephthalic acid, isophthalic acid, phthalic acid, itaconic acid, oxalic acid, 2,2'-thiodiacetic acid, 3,3'-thiodipropionic acid, admergic acid, 2,5-furandicarboxylic acid, cyclohexane-1,4-dicarboxylic acid, cyclohexane-1,2-dicarboxylic acid, phenylsuccinic acid, glutamic acid, aspartic acid, diglycolic acid and iminodiacetic acid, the radical $R^1$ is selected from the group consisting of hydrogen, branched or unbranched $C_1$- to $C_{30}$-alkyl radicals, branched or unbranched $C_1$- to $C_{30}$-alkenyl radicals, $C_7$- to $C_{30}$-arylalkyl radicals and/or $C_1$- to $C_{30}$-heteroarylalkyl radicals and $C_4$- to $C_{30}$-aryl radicals, the radical W is selected from the group consisting of —$CH_2$— and/or —CH=CH—, x is an integer from 1 to 20, preferably 1 to 10,
y is an integer from 1 to 20, preferably 1 to 10,
m is an integer from 1 to 10, preferably 1 to 5,
n is an integer from 1 to 10, preferably 1 to 5.

As radical Z, particular preference is given to using polyvalent carboxylic acids selected from the group consisting of hydrogenated or non-hydrogenated dimer acid, phthalic acid, oxalic acid, 2,2'-thiodiacetic acid, 3,3'-thiodipropionic acid, admergic acid, cyclohexane-1,4-dicarboxylic acid, cyclohexane-1,2-dicarboxylic acid, phenylsuccinic acid, diglycolic acid.

DESCRIPTION OF THE FIGURES

FIG. 1 shows the chemical structures of polyvalent carboxylic acids synthesized according to the present disclosure.

FIG. 2 shows the chemical structures of alcohols synthesized according to the resent disclosure.

FIG. 3 shows the chemical structures of polymer units synthesized according to the present disclosure.

DETAILED DESCRIPTION

The ester compounds of the general formula (I) and (II) according to the invention may be synthesized by the methods A, B and C described below. In method A, di-, tri- or higher functional carboxylic acids are reacted, under the effect of catalysts such as perchloric acid, with unsaturated fatty acids and subsequently esterified with alcohols.

Method A for preparing the ester compound according to the invention comprises the steps of:
(A) addition of a catalyst to a di-, tri- or higher functional carboxylic acid at 50 to 70° C. for a period of 30 minutes,
(B) addition of an unsaturated fatty acid to the mixture over a period of 4 to 8 hours, then the reaction mixture is stirred at 50 to 70° C. for 10 to 14 hours,
(C) the intermediate obtained is diluted with toluene/ether and washed repeatedly with water,
(D) esterification of the intermediate with an alcohol in the presence of a catalyst at 120 to 150° C. with stirring for 3 to 5 hours, wherein water formed and the residual water/ether in the organic phase are removed under reduced pressure, for example by means of a water separator,
(E) washing the crude product with aq. $NaHCO_3$ solution and water,
(F) drying over $Na_2SO_4$,
(G) purification of the crude product by means of a short-path evaporator under reduced pressure at 190 to 300° C.

The unsaturated fatty acid is preferably selected from the group consisting of oleic acid and/or erucic acid.

The alcohol is preferably selected from the group consisting of 2-ethylhexan-1-ol and/or 2-propylheptan-1-ol and/or 2-hexyldecan-1-ol and/or 2-octyldodecan-1-ol and/or isoamyl alcohol.

The catalyst used in reaction step (A) is preferably perchloric acid and in reaction step (D) is preferably p-toluenesulfonic acid.

It should also be noted that the further double bonds present in the compounds of the formulae (I) and (II) may react with carboxylic acids.

As alternative synthetic route according to method (B), long-chain fatty acids having hydroxyl groups are reacted under the effect of catalysts with di-, tri- or higher functional carboxylic acids and subsequently esterified.

This method B comprises the steps of:
(A) reacting a di-, tri- or higher functional carboxylic acid with a long-chain fatty acid having hydroxyl groups in the presence of a catalyst at 120 to 150° C.,
(B) reducing the pressure,
(C) portionwise or continuous addition of the long-chain fatty acid having hydroxyl groups over a period of 5 to 20 hours,
(D) stirring the reaction mixture obtained for 5 to 20 hours under reduced pressure and removing the water obtained, for example by means of a water separator,
(E) esterifying the intermediate with an alcohol at 120 to 150° C. for 3 to 5 hours with stirring,
(F) washing the crude product with aq. NaHCO₃ solution and water,
(G) drying over Na₂SO₄,
(H) purifying the crude product by means of a short-path evaporator under reduced pressure at 190 to 300° C.

The long-chain fatty acid having hydroxyl groups is preferably selected from 12-hydroxystearic acid and/or ricinoleic acid.

The alcohol is preferably selected from the group consisting of 2-ethylhexan-1-ol and/or 2-propylheptan-1-ol and/or 2-hexyldecan-1-ol and/or 2-octyldodecan-1-ol and/or isoamyl alcohol.

Preference is given to using p-toluenesulfonic acid as catalyst in reaction step (A).

A further preferred synthetic method is method C in which a long-chain fatty acid having hydroxyl group is reacted with an alcohol under the effect of catalysts and the intermediate obtained is esterified with a di-, tri- or higher functional carboxylic acid.

Method C comprises the steps of:
(A) reacting a long-chain fatty acid having hydroxyl groups with an alcohol in the presence of a catalyst at 60 to 90° C.,
(B) reducing the pressure,
(C) stirring the reaction mixture obtained over 6 to 10 hours under reduced pressure and removing the water obtained,
(D) removing the solvent and excess alcohol under vacuum,
(E) reacting the intermediate with a di-, tri- or higher functional carboxylic acid in the presence of a catalyst at 120 to 160° C. for 6 to 10 hours with stirring and removing the water obtained,
(F) removing the catalyst by (acid) washing of the crude product with aq. NaHCO₃ solution and water or by filtering off catalysts supported on supports or by evaporating volatile catalysts by applying a vacuum,
(G) drying over suitable drying agents, such as Na₂SO₄ for example,
(H) purifying the crude product under reduced pressure at 190 to 300° C., for example by means of a short-path evaporator.

The long-chain fatty acid having hydroxyl groups is preferably selected from 12-hydroxystearic acid and/or ricinoleic acid.

The alcohol is preferably selected from the group consisting of 2-ethylhexan-1-ol and/or 2-propylheptan-1-ol and/or 2-hexyldecan-1-ol and/or 2-octyldodecan-1-ol and/or isoamyl alcohol.

Preference is given to using p-toluenesulfonic acid as catalyst in reaction step (A) and (E).

All methods can be partly or completely adapted to alternative catalysts, for example catalysts based on enzymes.

Examples of the syntheses according to methods A, B and C:

Method A
Use of dimer acid and oleic acid
The dimer acid is depicted by the structural formula below in method A.
This synthetic scheme is a synthesis of a compound or oligomeric mixture in which perchloric acid is used as catalyst.
The reaction is not regioselective such that attachment can take place at both olefinic carbon atoms (C9 or C10; depicted by the circle in the figure below).
Furthermore, the attachment can also take place by rearrangement reactions at other carbon atoms (is not shown in the structural formula below).

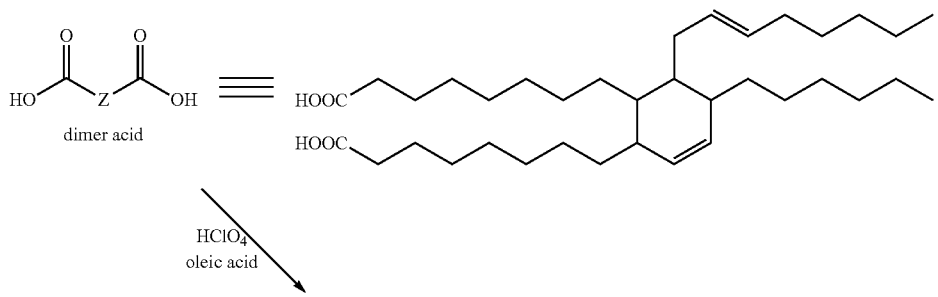

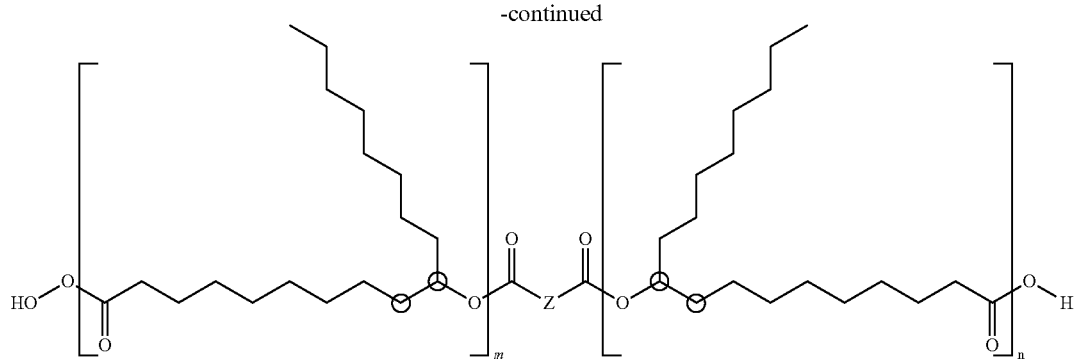

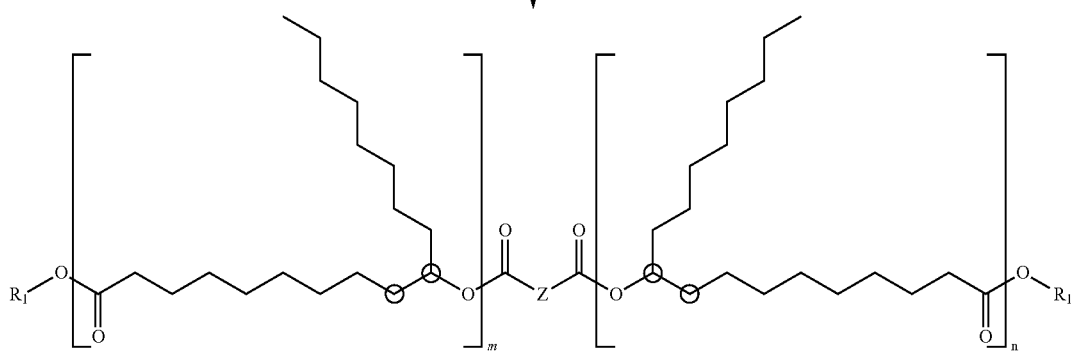

Method B

Use of a polyvalent carboxylic acid and 12-hydroxystearic acid and p-toluenesulfonic acid monohydrate (p-TsOH·H₂O) as catalyst.

Rearrangement reactions play no role in this method since the OH group is fixed at the C12 carbon.

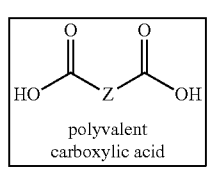

polyvalent carboxylic acid

↓ 12-hydroxystearic acid, p-TsOH·H₂O

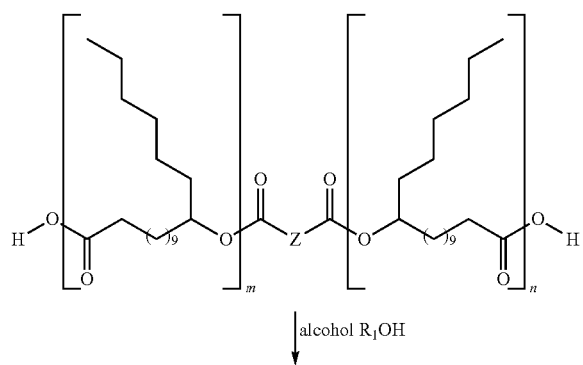

↓ alcohol R₁OH

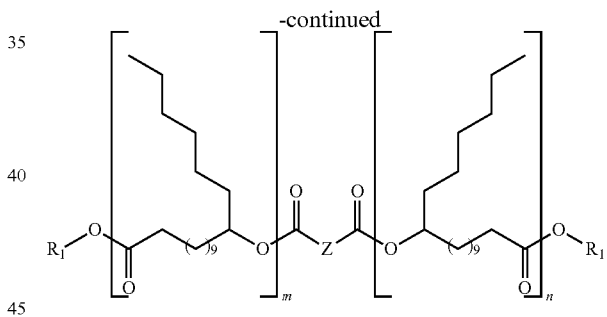

In method B, the polyvalent carboxylic acid used is a di-, tri- or higher functional carboxylic acid preferably selected from the group consisting of hydrogenated and non-hydrogenated dimer acid, trimer acid, 3,3'-thiodipropionic acid, 2,2'- thiodiacetic acid, diglycolic acid, itaconic acid, phenylsuccinic acid, phthalic anhydride, cyclohexane-1,2-dicarboxylic anhydride, cyclohexane-1,4-dicarboxylic acid.

2-Ethylhexan-1-ol (as R₁OH in the figures above) is preferably used for the esterification. Other alcohols may also be used.

For instance, isoamyl alcohol, Guerbet alcohol such as for example 2-hexyldecan-1-ol or 2-octyldodecan-1-ol, and 2-propylheptan-1-ol can be used.

Method C

Use of 12-hydroxystearic acid and p-toluenesulfonic acid monohydrate (p-TsOH·H₂O) as catalyst.

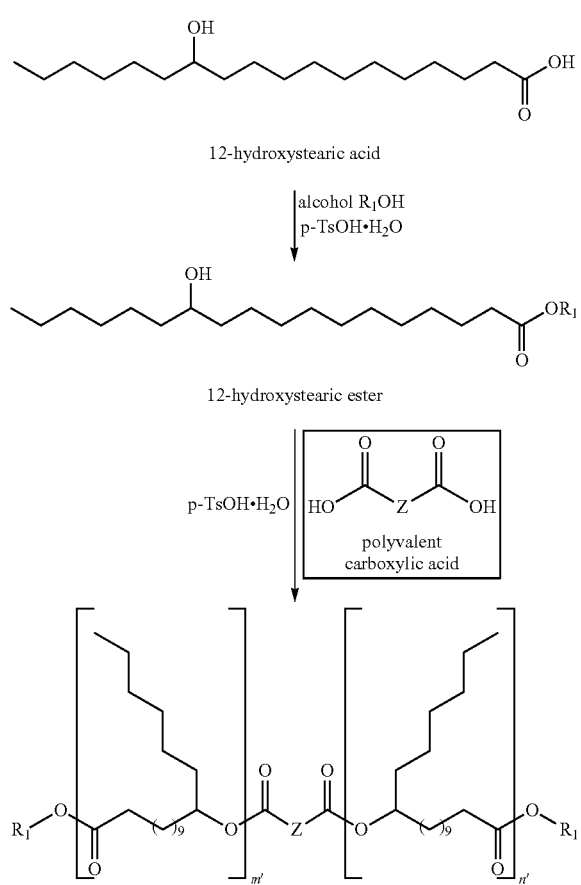

where m' is an integer from 0 to 10, preferably 0 to 5, n' is an integer from 0 to 10, preferably 0 to 5, and m'+n'≥1

As $R_1OH$, preference is given to using an alcohol selected from the group consisting of isoamyl alcohol, 2-ethylhexan-1-ol, 2-propylheptan-1-ol, 2-hexyldecan-1-ol, 2-octyldodecan-1-ol.

The polyvalent carboxylic acid is a di-, tri- or higher functional carboxylic acid preferably selected from the group consisting of hydrogenated or non-hydrogenated dimer acid, trimer acid, 3,3'-thiodipropionic acid, 2,2'-thiodiacetic acid, diglycolic acid, itaconic acid, phthalic anhydride.

In addition to 12-hydroxystearic acid, ricinoleic acid is also used as long-chain fatty acid having hydroxyl groups.

The novel ester compounds prepared by the method according to the invention are used in lubricant compositions.

Using the ester compounds according to the invention, lubricants can be provided which are used in a high temperature range, in the marine sector and in the food sector.

In addition to the novel ester compound, the lubricant compositions according to the invention may comprise further base oil components based on natural glyceride esters, preferably sunflower oil, rapeseed oil or colza oil, linseed oil, corn oil or corn zo germ oil, safflower oil, soybean oil, flaxseed oil, groundnut oil, "lesquerella" oil, palm oil, olive oil, in the monomeric, oligomeric and/or polymerized forms or mixtures of the oils mentioned.

Esters such as trimethylolpropane and pentaerythritol esters, and TMP complex esters, can be fully or partly esterified with saturated and/or mono- or polyunsaturated carboxylic acids of chain length 6 to 36 carbon atoms. These may be linear or branched.

Furthermore, it is also possible to use complex esters of dimer acids, dimer acid esters such as ethylhexyl dimerate, aliphatic carboxylic and dicarboxylic esters, and also phosphate esters, trimellitic and pyromellitic esters, ethers, polyether polyols and perfluoropolyethers, alkyl diphenyl ethers and polyphenyl ethers, silicone oils, polyglycols consisting of randomly distributed polyoxyethylene and/or polyoxypropylene units and/or other polyoxyalkylene components, and other glycol derivatives. The use of polyalphaolefins, including those prepared by metallocene catalysis, and alpha-olefin copolymers, is also possible.

Also possible is the use of polymeric systems, for example non-hydrogenated, partly hydrogenated or fully hydrogenated polyisobutylene or a mixture thereof, styrene and polystyrene and their derivatives and/or polymeric systems based on acrylates, acetate polymers and amides, polyethylenes, polypropylenes, halogenated polypropylenes and/or cycloalkanes.

Furthermore, it is possible to use mineral oils, for example white oil, alkylated diphenyl ethers, alkylated naphthalenes and perfluoropolyethers and silicone oils. The lubricant containing the ester compound according to the invention of the general formula (I) may be used either in the form of a lubricant oil or a lubricant grease.

The lubricant further comprises additives that are used individually or in combination and are selected from the group consisting of anticorrosion additives, antioxidants, antiwear additives, UV stabilizers, inorganic or organic solid lubricants, pour point and VI improvers, polymers, adhesion additives, dyes, emulsifiers, defoamers and solid lubricants that are typical for the formulation of a lubricant oil or lubricant grease.

Lubricant greases may be produced with different thickeners. One possible group of thickeners is that of ureas consisting of the reaction product of a diisocyanate, preferably 2,4-diisocyanatotoluene, 2,6-diisocyanatotoluene, 4,4'-diisocyanatodiphenylmethane, 2,4'-diisocyanatophenylmethane, 4,4'-diisocyanatodiphenyl, 4,4'-diisocyanato-3,3'-dimethylphenyl, 4,4'-diisocyanato-3,3'-dimethylphenylmethane, which may be used individually or in combination, with an amine of the general formula $R'_2$—N—R, or a diamine of the general formula $R'_2$—N—R—$NR'_2$, where R is an aryl, alkyl or alkylene radical having 2 to 22 carbon atoms and R' is identical or different and is a hydrogen, an alkyl, alkylene or aryl radical, or with mixtures of amines and diamines.

Further possible thickeners may be Al complex soaps, simple metal soaps of the elements of the first and second main groups of the Periodic Table, complex metal soaps of the elements of the first and second main groups of the Periodic Table, bentonites, sulfonates, silicates, aerosil, polyimides or PTFE or a mixture of the aforementioned thickeners.

In order to meet the legal requirements with regard to the use of lubricants for lubricating machinery for the processing of foods, it is appropriate when the additives and thickeners used have an H1 classification.

The addition of antioxidants can reduce or even prevent the oxidation of the oil or grease according to the invention, especially in the use thereof. The antioxidants are selected from the group consisting of aromatic diarylamines, phenols, thiophenols, phosphites, butylated hydroxytoluene, butylated hydroxyanisole, phenyl-alpha-naphthylamines, phenyl-beta-naphthylamines, octylated/butylated diphenylamines, di-alpha-tocopherol, benzenepropanoic acid and mixtures of these components.

The lubricant according to the invention may contain anticorrosion additives, metal deactivators or ion chelaters. These include triazoles, imidazolines, N-methylglycine (sarcosine), benzotriazole derivatives, N,N-bis(2-ethylhexyl)-ar-methyl-1 H-benzotriazole-1-methanamine; n-methyl-N-(1-oxo-9-octadecenyl)glycine, mixture of phosphoric acid and its mono- and diisooctyl esters reacted with (C11-14)-alkylamines, mixtures of phosphoric acid and mono- and diisooctyl esters reacted with tert-alkylamines and primary (C12-14) amines, dodecanoic acid, triphenyl phosphorothionate and amine phosphates. Such additives are commercially available under the names: IRGAMET® 39, IRGACOR® DSS G, Amin 0; SARKOSYL® O (Ciba), COBRATEC® 122, CUVAN® 303, VANLUBE® 9123, Cl-426, Cl-426EP, Cl-429 and Cl-498.

The lubricant according to the invention may additionally contain antiwear additives and friction modifiers. Antiwear additives are amines, amine phosphates, phosphates, thiophosphates, phosphorothionates, aryl phosphate, alkylated polysulfides, sulfurized amine compounds, sulfurized fatty acid methyl esters, naphthenic acids, nanoparticles selected from the groups of $Al_2O_3$, $SiO_2$, $TiO_2$, $ZrO_2$, $WO_3$, $Ta_2O_5$, $V_2O_5$, $CeO_2$, aluminum titanate, BN, $MoSi_2$, SiC, $Si_3N_4$, TiC, TiN, $ZrB_2$, clay minerals and/or mixtures thereof, and also thermally stable carbonates and/or sulfates, and mixtures of these components. The commercially available antiwear additives include IRGALUBE® TPPT, IRGALUBE® 232, IRGALUBE® 349, IRGALUBE® 211 and ADDITIN® RC3760 Liq 3960, FIRC-SHUN® FG 1505 and FG 1506, NA-LUBE® KR-015FG, LUBEBOND®, FLUORO® FG, SYNALOX® 40-D, ACHESON® FGA 1820 and ACHESON® FGA 1810.

The lubricant according to the invention may also contain pour point and viscosity improvers and adhesion additives. Pour point and viscosity improvers are selected from the group consisting of linear and/or branched alkylated, acrylated and aliphatic polymers and copolymers, and polymerized fatty acid esters, and from the group of PIBs (polyisobutylenes) and PBs (polybutenes) in partly or fully hydrogenated form.

The lubricant according to the invention may contain UV stabilizers. UV stabilizers are selected from the group consisting of nitrogen heterocycles, substituted nitrogen heterocycles, linear and branched alkylated, acylated, aliphatic nitrogen heterocycles, and derivatives thereof.

The lubricant according to the invention may contain solid lubricants. Solid lubricants are e.g. PTFE, BN, pyrophosphate, Zn oxide, Mg oxide, pyrophosphates, thiosulfates, Mg carbonate, Ca carbonate, Ca stearate, Zn sulfide, Mo sulfide, W sulfide, Sn sulfide, graphite, graphene, nanotubes, $SiO_2$ polymorphs or a mixture thereof.

The lubricant according to the invention may contain emulsifiers. Emulsifiers are selected from the group consisting of branched and/or linear ethoxylated and/or propoxylated alcohols and salts thereof, such as for example alcohols, C16-C18, zo ethoxylated, propoxylated, polyglycols, fatty acid esters, silicates, ionic surfactants, such as for example sodium salts of alkylsulfonic acids, where the chains contain C14-17 carbons.

The lubricant according to the invention may contain defoamers. Defoamers are selected from the group consisting of ethoxylated and/or propoxylated alcohols of chain lengths C10-C18, mono- and diglycerides of cooking fats, acrylates, propoxylated and/or ethoxylated alkyl ethers (polyglycols), alcohols, siloxanes.

The lubricant compositions according to the invention based on the ester compound of the general formulae (I) or (II) are used in the marine sector, in the inland waterways sector and in offshore facilities, i.e. for lubricating chains, ball bearings, propeller rudders, propeller shafts, machine components and facilities that come into contact with saltwater in the marine sector or with water and aqueous media in inland waterways. Furthermore, they are used in the lubrication of machinery in the food processing industry, as hydraulic oil in the food processing industry, for transport and control chains, for apparatuses for the processing of cereal, flour and animal feed, and in baking ovens. They are also used for lubricating bearings and slide bearings, transport and control chains in vehicle technology, in conveying technology, in mechanical engineering, in office technology and in industrial plants and machinery, and in the sectors of domestic appliances and consumer electronics. Furthermore, they are used for lubricating bevel gears and spur gears of roller bearings in continuous casting plants and transport bearings in continuous kilns and for open crown gear lubrication in rotary kilns, tubular mills, drums and mixers, such as specifically in the cement, lime, gypsum, mining and chemical industries.

The ester compounds according to the invention and the preparation thereof and use thereof in a lubricant composition are now elucidated by way of the following examples.

EXAMPLES

Example 1

Synthesis of the ester Compound
Method A:

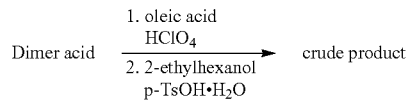

$HClO_4$ solution (70% in water, 60 g) was added to dimer acid (100 g, Pripol 1013, CRODA) and the mixture was heated to 60° C. for 30 min. Oleic acid (500 g, Radiacid 0137, OLEON) was added dropwise at 60° C. over a period of 4.5 hours. The reaction mixture was then stirred at 60° C. for 13 h. After cooling, the product was diluted with toluene (300 ml) and diethyl ether (100 ml) and washed with water (7×600 ml). 2-Ethylhexan-1-ol (250 g) and p-toluenesulfonic acid monohydrate (3 g) were added to the organic phase and the solution was stirred at 125° C. for 5 h. The amount of water formed and the residual water/ether in the organic phase were removed by means of a water separator. Reduced pressure was applied in order to accelerate the distillation process. The reaction mixture was then washed with 4% aq. $NaHCO_3$ solution (2×400 ml), and water (300 ml) dried over $Na_2SO_4$ and concentrated under reduced pressure. The crude product was fractionally distilled using a short-path evaporator.

2-Propylheptan-1-ol, 2-hexyldecan-1-ol (ISOFOL 16), 2-octyldodecan-1-ol (ISOFOL 20) and isoamyl alcohol were also used in place of 2-ethylhexan-1-ol.

Erucic acid may be used in place of oleic acid.

Method B:

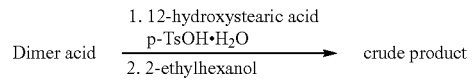

12-Hydroxystearic acid (90 g, 12-HSA) and p-toluenesulfonic acid monohydrate (12.0 g) were added to dimer acid (90 g, Pripol 1013, CRODA) and the mixture was heated to 135° C. The pressure was reduced to accelerate the distillation process and 12-HSA (90 g) was added 5 times after every 1.5 hours. The reaction mixture was stirred at 135° C. under reduced pressure and the amount of water formed (27.4 ml) was removed by means of a water separator. After addition of the last portion of 12-HSA, the reaction mixture was stirred at 135° C. under reduced pressure for 10 h. 2-Ethylhexan-1-ol (150 g) was then added and the mixture stirred at 135° C. for 5 h. After cooling, the reaction mixture was washed with 4% aq. NaHCO$_3$ solution (500 ml) and water (3×500 ml), dried over Na$_2$SO$_4$ and concentrated under reduced pressure. The crude product was fractionally distilled using a short-path evaporator.

2-Propylheptan-1-ol, 2-hexyldecan-1-ol (ISOFOL 16), 2-octyldodecan-1-ol (ISOFOL 20) and isoamyl alcohol were also used in place of 2-ethylhexan-1-ol.

Ricinoleic acid may also be used in place of 12-hydroxystearic acid.

Method C:

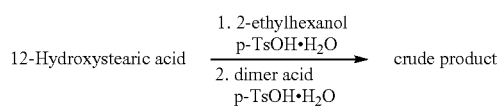

A mixture of 12-hydroxystearic acid (500 g, 1.66 mol, 1.00 eq.), 2-ethylhexanol (542 g, 4.16 mol, 2.50 eq.) and p-TsOH·H$_2$O (6.33 g, 33.3 mmol, 2 mol%) in cyclohexane (600 ml) was stirred at an oil bath temperature of 85° C. for 7.5 h in a Dean-Stark apparatus. Slight negative pressure was applied and the water formed by esterification (total 30 ml) was rapidly distilled over. The reaction mixture was filtered through filter paper, washed with aqueous NaHCO$_3$ solution (6% by weight, 300 ml) and water (2×300 ml), dried over Na$_2$SO$_4$ and concentrated under reduced pressure. The crude product was distilled off under vacuum at 0.1 mbar, T$_{oil\ bath}$=110° C. and the residue (670 g) was stored as intermediate for the next step.

A mixture of dimer acid (Pripol 1013, Croda, 50 g), intermediate from the first step (12-HSA ester, 104 g) and p-TsOH monohydrate (2.5 g) in toluene (150 ml) was stirred at an oil bath temperature of 150° C. for 8 h in a Dean-Stark apparatus. The water formed (total 3.6 ml) was distilled over. The reaction mixture was diluted with diethyl ether (50 ml), washed with aqueous NaHCO$_3$ solution (5% by weight, 2×100 ml) and water (2×100 ml), dried over Na$_2$SO$_4$ and concentrated under reduced pressure. The crude product was fractionally distilled using a short-path evaporator.

2-Propylheptan-1-ol, 2-hexyldecan-1-ol (ISOFOL 16), 2-octyldodecan-1-ol (ISOFOL 20) and isoamyl alcohol were also used in place of 2-ethylhexan-1-ol.

Ricinoleic acid may also be used in place of 12-hydroxystearic acid. The crude products obtained were purified, as already described, using a short-path evaporator (Model VKL 70-4 FDRR-SKR-T from VTA) with application of a suitable vacuum and the distillation conditions optimized by means of GPC analysis. In the 1$^{st}$ distillation step at 200° C., solvent and unreacted alcohol were removed. In the 2$^{nd}$ distillation, the temperature should not exceed 300° C., since ester pyrolysis occurs at this temperature.

For the following novel ester compounds, the chemical and physical properties were tested and these are shown in Table 1.

Compound (1) is the reaction product of dimer acid/oleic acid/2-ethylhexan-1-ol, Compound (2) is the reaction product of dimer acid/oleic acid/ISOFOL 16, Compound (3) is the reaction product of dimer acid/oleic acid/ISOFOL 20, Compound (4) is the reaction product of dimer acid/12-HSA/2-ethylhexan-1-ol, Compound (5) is the reaction product of 12-HSA/2-ethylhexan-1-ol/dimer acid, in which the compounds (1) to (3) were prepared according to method A, the compound (4) according to method B and the compound (5) according to method C.

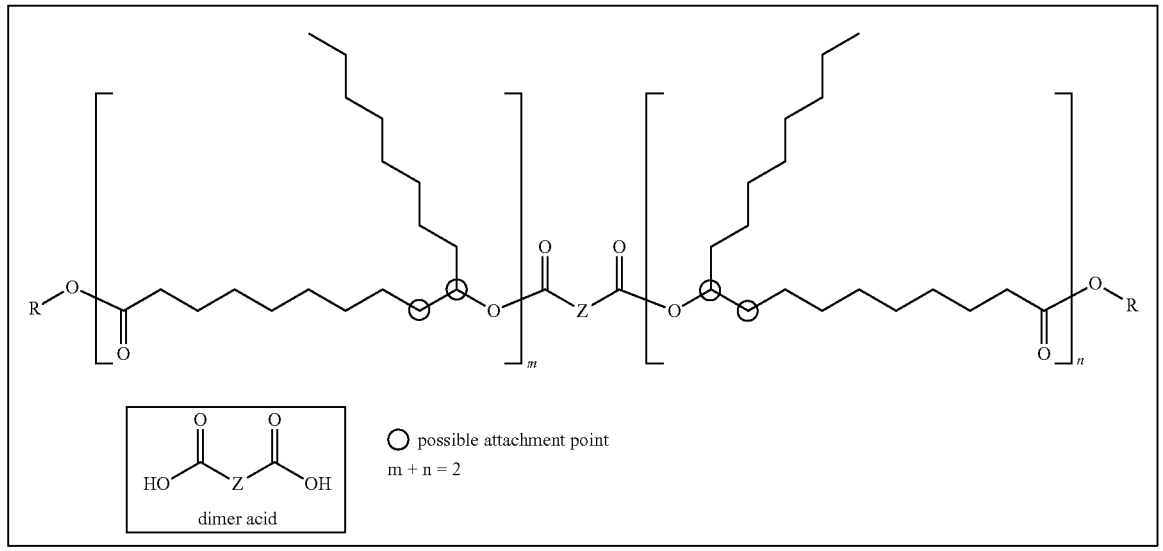

-continued
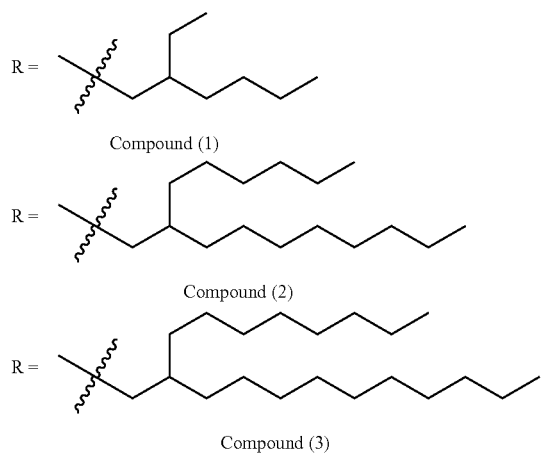
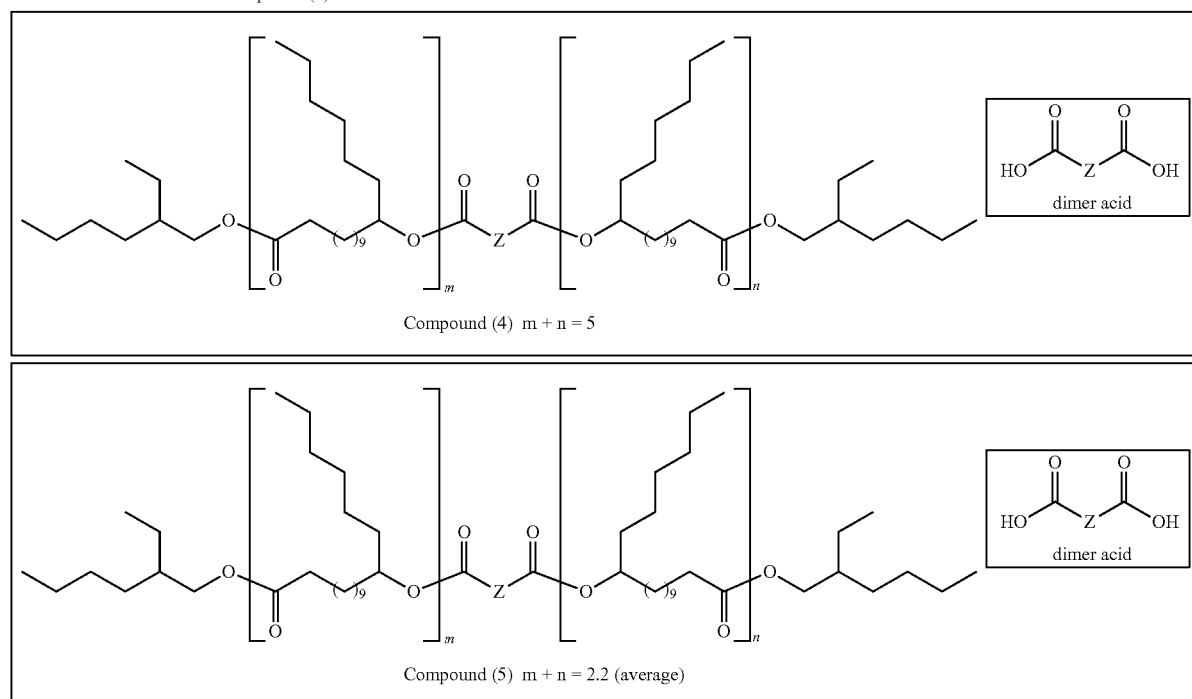
TABLE 1
Chemical and physical properties of the compounds (1) to (5)
| Parameter | Method | Unit | (1) | (2) | (3) | (4) | (5) |
|---|---|---|---|---|---|---|---|
| Appearance | | | liquid clear brown | liquid clear brown | liquid clear brown | liquid clear brown | liquid clear brown |
| Kin. Vis. 40° C. | ASTM | mm$^2$/s | 202 | 300 | 261 | 497 | 275 |
| Kin. Vis. 100° C. | D 7042 | | 25 | 35 | 32 | 54 | 32 |
| VI | | | 157 | 160 | 163 | 174 | 159 |
| Neutralization number | DIN 51558 | mg KOH/g | 1.3 | 1.6 | 1.1 | 0.65 | 0.55 |
| Pour point | DIN ISO 3016 | ° C. | −30 | −45 | −39 | −24 | −42 |
| Biodegradability | OECD 301 F | % | 50.9 | 50.2 | 60 | 66.8 | 45.6 |

TABLE 2

Comparative examples of compounds (A) to (C)

| Parameter | Method | Unit | Ester A | Ester B | Ester C |
|---|---|---|---|---|---|
| Biodegradability | OECD 301 F | % | 30.2 | 25.0 | 34.2 |

Ester A: Diester of dimer acid/2-ethylhexan-1-ol
Ester B: diester of dimer acid/amyl alcohol
Ester C: diester of dimer acid/ISOFOL 16.

The comparison of compounds (1) to (3) shows that better biodegradability is attained the greater the molecular proportion of alcohol. Moreover, it is clear from Table 2 that pure diesters (=compounds A to C) of dimer acid and the alcohols used are non-biodegradable according to OECD 301 F. The biodegradability of the ester can be significantly increased by appropriate modification with oleic acid or 12-HSA (=compounds (1) to (4)) (compare Table 1 and 2).

It has also been shown that compound (4), which was prepared according to method B, had the best chemical and physical properties.

TABLE 3

Beverage bottle test ASTM D 2619 (unit: TAN [mg KOH/g], kin. visc. [mm$^2$/s])

| Product | TAN aq. phase | TAN oil before | TAN oil after | Δ TAN oil | Visc. oil 40° C. before | Visc. oil 40° C. after | Δ Visc. oil 40° C. |
|---|---|---|---|---|---|---|---|
| (1) | 1.32 | 1.3 | 4.3 | 3 | 201 | 196 | −5 |
| (3) | 0.59 | 1.1 | 2.3 | 1.2 | 261 | 254 | −7 |
| (4) | 1.1 | 0.65 | 1.56 | 0.91 | 497 | 473 | −24 |
| Reference ester | 3 | 0.2 | 12.9 | 12.7 | 963.1 | 650.8 | −312.3 |

Reference ester: 1,1,1-trimethylolpropane (TMP) ester saturated; biodegradable; ISO VG 1000, The beverage bottle test is used to determine the resistance to hydrolysis of lubricants and base oils. Table 3 shows that products (1), (3) and (4) according to the invention are highly stable to hydrolysis compared to the reference ester. The acid number and the kinematic viscosity change significantly less.

Further ester compounds were synthesized from various polyvalent carboxylic acids (see FIG. 1), alcohols R$_1$OH (see FIG. 2) and two polymer units (see FIG. 3) io and these are shown in Table 4 (method B) and Table 5 (method C). The chemical and physical properties are shown in Table 6.

TABLE 4

Ester compounds according to method B with 12-HSA as polymer unit

| | Alcohols R$_1$OH (see FIG. 2) | | | | |
|---|---|---|---|---|---|
| | A1 | A2 | A3 | A4 | A5 |
| Dimer acid (S1) | (6) | (4)/(19)* | (20)* | (7)/(21)* | (8) |
| hyd. Dimer acid (S2) | | (9) | | | |
| Trimer acid (S3) | | (10) | | | |
| 3,3'-Thiodipropionic acid (S4) | | (11) | | | |
| 2,2'-Thiodiacetic acid (S5) | | (12) | | | |
| Diglycolic acid (S6) | | (13) | | | |
| Itaconic acid (S7) | | (14) | | | |
| Phenylsuccinic acid (S8) | | (15) | | | |
| Phthalic anhydride (S9) | | (16) | | | |
| Cyclohexane-1,2-dicarboxylic anhydride (S10) | | (17) | | | |
| Cyclohexene-4,5-dicarboxylic anhydride (S11) | | (18) | | | |

*in compound (19), (20) and (21) ricinoleic acid was used in place of 12-HSA.
A1 = isoamyl alcohol,
A2 = 2-ethylhexan-1-ol,
A3 = 2-propylheptan-1-ol,
A4 = 2-hexyldecan-1-ol,
A5 = 2-octyldodecan-1-ol

TABLE 5

Ester compounds according to method C with 12-HSA as polymer unit

| | Alcohols R$_1$OH (see FIG. 2) | | | | |
|---|---|---|---|---|---|
| | A1 | A2 | A3 | A4 | A5 |
| Dimer acid (S1) | | (5)/(28)* | | (22) | |
| hyd. Dimer acid (S2) | | | | | |
| Trimer acid (S3) | | (23)/(29)* | | | |
| 3,3'-Thiodipropionic acid (S4) | | (24)/(30)* | | (25) | |
| 2,2'-Thiodiacetic acid (S5) | | (26)/(31)* | | (27) | |
| Diglycolic acid (S6) | | | | | |

*in compound (28), (29), (30) and (31), ricinoleic acid was used in place of 12-HSA.
A1 = isoamyl alcohol,
A2 = 2-ethylhexan-1-ol,
A3 = 2-propylheptan-1-ol,
A4 = 2-hexyldecan-1-ol,
A5 = 2-octyldodecan-1-ol The molar ratio remains as in Example 1 according to methods A, B and C.

TABLE 6

Chemical and physical properties of compounds (6) to (31)

| | Parameter | | | | |
|---|---|---|---|---|---|
| | Kin. Vis. at 40° C. | Kin. Vis. at 100° C. | VI Method | Neutralization number | Pour point |
| | ASTM D7042 | | | DIN 51558 | DIN ISO 3016 |
| Unit | mm²/s | mm²/s | | mg KOH/g | ° C. |
| Compound (6) | 473 | 53 | 177 | 0.2 | −21 |
| Compound (7) | 516 | 56 | 176 | 0.4 | −30 |
| Compound (8) | 578 | 63 | 181 | 0.7 | −30 |
| Compound (9) | 507 | 56 | 177 | 0.2 | −27 |
| Compound (10) | 568 | 61 | 178 | 0.6 | −24 |
| Compound (11) | 349 | 42 | 175 | 0.4 | −27 |
| Compound (12) | 322 | 38 | 170 | 0.3 | −24 |
| Compound (13) | 305 | 36 | 168 | 0.4 | −21 |
| Compound (14) | 318 | 33 | 169 | 0.4 | −24 |
| Compound (15) | 387 | 44 | 170 | 0.5 | −27 |
| Compound (16) | 452 | 50 | 173 | 0.5 | −24 |
| Compound (17) | 390 | 44 | 171 | 0.4 | −24 |
| Compound (18) | 403 | 46 | 172 | 0.4 | −24 |
| Compound (19) | 337 | 43 | 183 | 0.3 | −51 |
| Compound (20) | 376 | 46 | 181 | 0.5 | −51 |
| Compound (21) | 395 | 48 | 183 | 0.4 | −51 |
| Compound (22) | 306 | 34 | 155 | 1.0 | −48 |
| Compound (23) | 500 | 51 | 162 | 1.4 | −45 |
| Compound (24) | 108 | 16 | 158 | 1.0 | −42 |
| Compound (25) | 142 | 19 | 154 | 0.6 | −39 |
| Compound (26) | 107 | 16 | 153 | 1.5 | −42 |
| Compound (27) | 141 | 19 | 150 | 0.6 | −54 |
| Compound (28) | 230 | 29 | 164 | 0.5 | −51 |
| Compound (29) | 404 | 45 | 167 | 1.1 | −48 |
| Compound (30) | 106 | 16 | 167 | 0.7 | −60 |
| Compound (31) | 103 | 16 | 162 | 0.7 | −60 |

The table shows that excellent low temperature properties (see PP) can be achieved.

Emphasis is given to compounds 19 to 21 which, despite high viscosity at 40° C., exhibit very low pour points. Also noteworthy are the high viscosity indices (VI) throughout.

Example 2

Preparation of a Lubricant Grease

The novel ester (compound 1) was further thickened with 15% Li complex thickener and 4% antioxidant was added. The exact composition is specified in Table 7.

The lubricant grease is produced according to procedures known to those skilled in the art: the thickener is formed by an in situ reaction of the reactants used in the base oil. The mixture is then heated to from 150° C. to 210° C., stirred for several hours and cooled again. During the cooling process, the necessary additives are added at ca. 60° C. A homogeneous mixture of the grease is obtained by the final homogenization step by means of a roller, colloid mill or Gaulin homogenizer.

The particular stability to hydrolysis of the base oil enables the in situ preparation of the soap thickener.

TABLE 7

| Component | Compound (1) | 12-HSA | Azelaic acid | LiOH•H₂O | Antioxidant |
|---|---|---|---|---|---|
| Proportion | 80.99% | 9.55% | 2.87% | 2.59% | 4.00% |

The chemical and physical properties of the grease obtained were investigated and the results are presented in Table 8. It has the properties of typical Li complex grease, for example a dropping point of >300° C. Results of the corrosive effect on copper, water resistance and noise test are very good. Oil separation at high temperatures is also very good/low.

TABLE 8

Chemical and physical properties of the lubricant grease of Example 2

| Method name standard | Conditions | Parameter | Lubricant grease Ex. 2 |
|---|---|---|---|
| Flow pressure DIN 51805 | Temperature: −30° C. | Flow pressure (mbar) | 650 |
| | Temperature: −35° C. | | 1525 |
| Cone penetration DIN ISO 2137 | Number of double cycles: 60 Temperature: 25° C. Cone: standard cone | Penetration depth: (0.1 mm) | 283 |
| Corrosiveness to copper DIN 51811 | Time: 24 h Temperature: 150° C. | Degree of corrosion | 1a |
| Neutralization number DIN 51558 | Measurement time point: after saponification of 12-HSA and azelaic acid | Neutralization number (mg KOH/g) | 0.9630 |
| Oil separation ASTM D 6184 | Time: 30 h Temperature: 150° C. | Oil separation (%) | 3.02 2.83 3.13 |
| Oil separation ASTM D 6184 | Time: 30 h Temperature: 180° C. | Oil separation (%) | 4.60 3.91 |
| Oil separation DIN 51817 | Time: 168 h Temperature: 40° C. | Oil separation (%) | 1.91 1.87 |
| Dropping point DIN ISO 2176 | | Dropping point (° C.) | 344.7 |
| Evaporation loss DIN 58397 T1 | Time: 24 h Temperature: 150° C. | Evaporation loss (%) | 1.25 1.40 |
| Water resistance DIN 51807 Part 1 | Time: 3 h Temperature: 90° C. | Evaluation level | 0-90 |
| Shear viscosity | Original After storage at 150° C., 24 h | (mPa · s) | 4991 4310 4270 |

The invention claimed is:

1. An ester compound of the general formula (I):

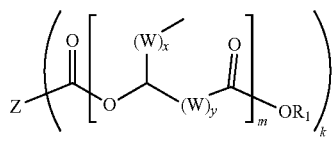

(I)

in which
the radical Z is selected from the group including hydrogenated or non-hydrogenated dimer acid, hydrogenated or non-hydrogenated trimer acid, 2,2'-thiodiacetic acid, and 3,3'-thiodipropionic acid,
the radical $R_1$ is selected from the group consisting of, branched or unbranched C1- to C30-alkyl radicals, branched or unbranched C1- to C30-alkenyl radicals, C7- to C30-arylalkyl radicals, C1- to C30-heteroarylalkyl radicals and C4- to C30-aryl radicals,
the radical W is selected from the group consisting of —$CH_2$— and CH=CH—,
x is an integer from 1 to 20,
y is an integer from 1 to 20,
m is an integer from 1 to 10,
k is an integer from 2 to 10.

2. An ester compound of a general formula (I)

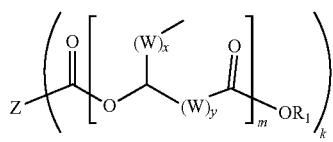

(I)

in which
the radical Z is selected from the group including phthalic acid, oxalic acid, admergic acid, 2,5-furandicarboxylic acid, cyclohexane-1,4-dicarboxylic acid, cyclohexane-1,2-dicarboxylic acid, and phenylsuccinic acid,
the radical $R_1$ is selected from the group consisting of branched or unbranched C1- to C30 -alkyl radicals, branched or unbranched C1- to C30-alkenyl radicals, C7- to C30-arylalkyl radicals, C1- to C30-heteroarylalkyl radicals and C4- to C30-aryl radicals,
the radical W is selected from the group consisting of —$CH_2$—and/or CH=CH—,
x is an integer from 1 to 20,
y is an integer from 1 to 20,
m is an integer from 1 to 10,
k is an integer from 2 to 10.

3. An ester compound having a general formula (II)

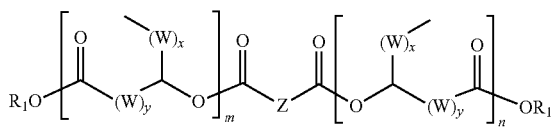

(II)

in which
the radical Z is selected from the group including hydrogenated or non-hydrogenated dimer acid, 2,2'-thiodiacetic acid, and 3,3'-thiodipropionic acid,
the radical $R^1$ is selected from the group consisting of branched or unbranched $C_1$- to $C_{30}$-alkyl radicals, branched or unbranched $C_1$- to $C_{30}$-alkenyl radicals, $C_7$- to $C_{30}$-arylalkyl radicals, and $C_1$- to $C_{30}$-heteroarylalkyl radicals and $C_4$- to $C_{30}$-aryl radicals,
the radical W is selected from the group consisting of —$CH_2$- and —CH=CH—,
x is an integer from 1 to 20,
y is an integer from 1 to 20,
m is an integer from 1 to 10,
n is an integer from 1 to 10.

4. An ester compound having a general formula (II)

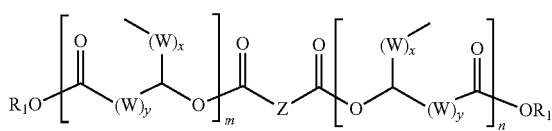

(II)

in which
the radical Z is selected from the group including phthalic acid, oxalic acid, admergic acid, cyclohexane-1,4-dicarboxylic acid, cyclohexane-1,2-dicarboxylic acid, and phenylsuccinic acid,
the radical $R_1$ is selected from the group consisting of branched or unbranched $C_1$- to $C_{30}$-alkyl radicals, branched or unbranched $C_1$- to $C_{30}$-alkenyl radicals, $C_7$- to $C_{30}$-arylalkyl radicals and $C_1$- to $C_{30}$-heteroarylalkyl radicals and $C_4$- to $C_{30}$-aryl radicals,
the radical W is selected from the group consisting of —$CH_2$- and —CH=CH—,
x is an integer from 1 to 20,
y is an integer from 1 to 20,
m is an integer from 1 to 10,
n is an integer from 1 to 10.

5. A method for producing an ester compound of the general formula (I)

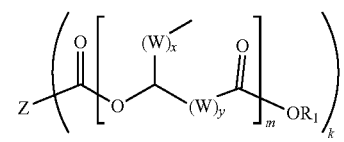

or of the general formula (II)

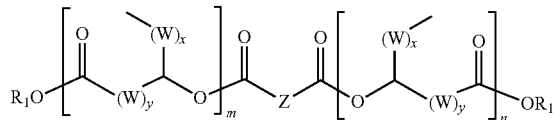

in which
the radical Z for general formula (I) is selected from the group including hydrogenated or non-hydrogenated dimer acid, hydrogenated or non-hydrogenated trimer acid, 2,2'- thiodiacetic acid, and 3,3'-thiodipropionic acid,
the radical Z for the general formula (II) is selected from the group including hydrogenated or non-hydrogenated dimer acid, 2,2'- thiodiacetic acid, and 3,3'-thiodipropionic acid,
the radical $R_1$ is selected from the group consisting of branched or unbranched $C_1$- to $C_{30}$-alkyl radicals, branched or unbranched $C_1$- to $C_{30}$-alkenyl radicals, $C_7$- to $C_{30}$-arylalkyl radicals, $C_1$- to $C_{30}$-heteroarylalkyl radicals and $C_4$- to $C_{30}$-aryl radicals,
the radical W is selected from the group consisting of —$CH_2$- and —CH=CH—,
x is an integer from 1 to 20,
y is an integer from 1 to 20,
m is an integer from 1 to 10,
k is an integer from 2 to 10, and
n is an integer from 1 to 10,
obtainable by;
(A) reacting a di-, tri- or higher functional carboxylic acid with a long-chain fatty acid having hydroxyl groups in the presence of a catalyst at 120 to 150° C., period of 30 minutes,
(B) reducing the pressure,
(C) portionwise or continuous addition of the long-chain fatty acid having hydroxyl groups over a period of 5 to 20 hours,
(D) stirring the reaction mixture obtained for 5 to 20 hours under reduced pressure and removing the water obtained,
(E) esterifying the intermediate with an alcohol at 120 to 150° C. for 3 to 5 hours with stirring,
(F) washing the crude product with aq. $NaHCO_3$ solution and water,
(G) drying over $Na_2SO_4$,
(H) purifying the crude product by means of a short-path evaporator under reduced pressure at 190 to 300° C.

6. The method for producing the ester compound of the general formula (I) or (II) as claimed in claim 5, in which the long-chain fatty acid having hydroxyl groups is selected from 12-hydroxystearic acid and/or ricinoleic acid; the alcohol is selected from the group consisting of 2-ethylhexan-1-ol and/or 2-propylheptan-1-ol and/or 2-hexyldecan-1-ol and/or 2-octyldodecan-1-ol and/or isoamyl alcohol; the catalyst in reaction step (A) is p-toluenesulfonic acid.

7. A method for producing ester compounds of the general formula (I)

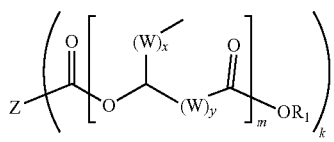

or of the general formula (II),

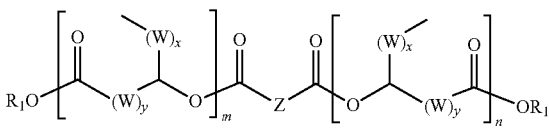

in which
the radical Z for general formula (I) is selected from the group including hydrogenated or non-hydrogenated dimer acid, hydrogenated or non-hydrogenated trimer acid, 2,2'- thiodiacetic acid, and 3,3'-thiodipropionic acid,
the radical Z for the general formula (II) is selected from the group including hydrogenated or non-hydrogenated dimer acid, 2,2'- thiodiacetic acid, and 3,3'-thiodipropionic acid,
the radical $R_1$ is selected from the group consisting of branched or unbranched $C_1$- to $C_{30}$-alkyl radicals, branched or unbranched $C_1$- to $C_{30}$-alkenyl radicals, $C_7$- to $C_{30}$-arylalkyl radicals, $C_1$- to $C_{30}$-heteroarylalkyl radicals and $C_4$- to $C_{30}$-aryl radicals,
the radical W is selected from the group consisting of —$CH_2$- and/or —CH=CH—,
x is an integer from 1 to 20,
y is an integer from 1 to 20,
m is an integer from 1 to 10,
k is an integer from 2 to 10, and
n is an integer from 1 to 10,
obtainable by;
(A) reacting a long-chain fatty acid having hydroxyl groups with an alcohol in the presence of a catalyst at 60 to 90° C.,
(B) reducing the pressure,
(C) stirring the reaction mixture obtained over 6 to 10 hours under reduced pressure and removing the water obtained,
(D) removing the solvent and excess alcohol under vacuum,
(E) reacting the intermediate with a di-, tri- or higher functional carboxylic acid in the presence of a catalyst at 120 to 160° C. for 6 to 10 hours with stirring and removing the water obtained,
(F) removing the catalyst by (acid) washing of the crude product with aq. $NaHCO_3$ solution and water or by filtering off catalysts supported on supports or by evaporating volatile catalysts by applying a vacuum,
(G) drying over suitable drying agents, such as $Na_2SO_4$, (H) purifying the crude product under reduced pressure at 190 to 300° C., for example by means of a short-path evaporator.

8. The method for producing ester compounds of the general formula (I) or (II) as claimed in claim 7, in which the long-chain fatty acid having hydroxyl groups is selected from 12-hydroxystearic acid and/or ricinoleic acid; the alcohol is selected from the group consisting of 2-ethylhexan-1-ol and/or 2-propylheptan-1-ol and/or 2-hexyldecan-1-ol and/or 2-octyldodecan-1-ol and/or isoamyl alcohol; the catalyst in reaction step (A) and (E) is p-toluenesulfonic acid.

9. A lubricant composition comprising an ester compound of the general formula (I)

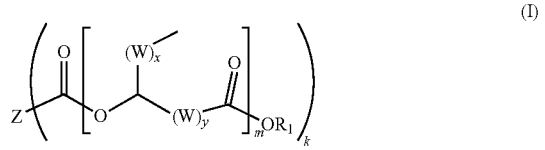

or of the general formula (II)

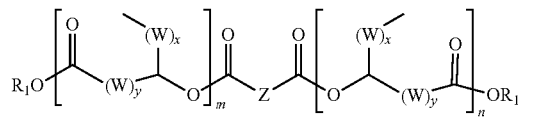

in which
    the radical Z for general formula (I) is selected from the group including hydrogenated or non-hydrogenated dimer acid, hydrogenated or non-hydrogenated trimer acid, 2,2'- thiodiacetic acid, and 3,3'-thiodipropionic acid,
    the radical Z for the general formula (II) is selected from the group including hydrogenated or non-hydrogenated dimer acid, 2,2'- thiodiacetic acid, and 3,3'-thiodipropionic acid,
    the radical $R_1$ is selected from the group consisting of branched or unbranched $C_1$- to $C_{30}$-alkyl radicals, branched or unbranched $C_1$- to $C_{30}$-alkenyl radicals, $C_7$- to $C_{30}$-arylalkyl radicals, $C_1$- to $C_{30}$-heteroarylalkyl radicals and $C_4$- to $C_{30}$-aryl radicals,
    the radical W is selected from the group consisting of —$CH_2$- and/or —CH=CH—,
    x is an integer from 1 to 20,
    y is an integer from 1 to 20,
    m is an integer from 1 to 10,
    k is an integer from 2 to 10, and
    n is an integer from 1 to 10.

10. The lubricant composition as claimed in claim 9 used in the marine sector, for lubricating machinery in the food processing industry, for lubricating ball bearings and slide bearings, transport and control chains in vehicle technology, in conveyor technology, mechanical engineering, in office technology for lubricating bevel gears and spur gears, of roller bearings in continuous kilns and for open crown gear lubrication in rotary kilns, tubular mills, drums and mixers in the cement, lime, gypsum, mining and chemical industries.

11. The-lubricant composition as claimed in claim 9, further comprising a base oil, solid lubricants and additives.

12. The lubricant composition as claimed in claim 9, further comprising a thickener.

13. A method for using a lubricant compositions based on ester compounds of the general formula (I)

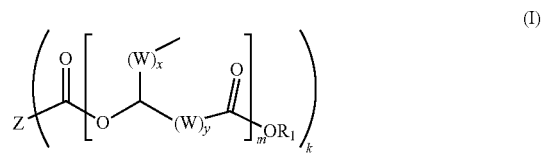

or of the general formula (II)

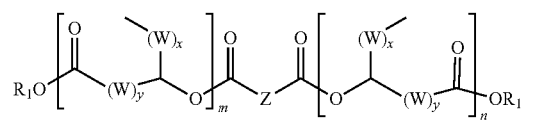

in which
    the radical Z for general formula (I) is selected from the group including hydrogenated or non-hydrogenated dimer acid, hydrogenated or non-hydrogenated trimer acid, 2,2'- thiodiacetic acid, and 3,3'-thiodipropionic acid,
    the radical Z for the general formula (II) is selected from the group including hydrogenated or non-hydrogenated dimer acid, 2,2'- thiodiacetic acid, and 3,3'-thiodipropionic acid,
    the radical $R_1$ is selected from the group consisting of branched or unbranched $C_1$- to $C_{30}$-alkyl radicals, branched or unbranched $C_1$- to $C_{30}$-alkenyl radicals, $C_7$- to $C_{30}$-arylalkyl radicals, $C_1$- to $C_{30}$-heteroarylalkyl radicals and $C_4$- to $C_{30}$-aryl radicals,
    the radical W is selected from the group consisting of —$CH_2$- and/or —CH=CH—,
    x is an integer from 1 to 20,
    y is an integer from 1 to 20,
    m is an integer from 1 to 10,
    k is an integer from 2 to 10, and
    n is an integer from 1 to 10;
    comprising lubricating components in the marine sector, lubricating machinery in the food processing industry, lubricating ball bearings and slide bearings, transport and control chains in vehicle technology, lubricating components in conveyor technology, lubricating components in mechanical engineering, lubricating components in office technology, lubricating bevel gears and spur gears, lubricating roller bearings in continuous casting plants, lubricating transport bearings in continuous kilns and lubricating open crown gear lubrication in rotary kilns, tubular mills, drums and mixers in the cement, lime, gypsum, mining and chemical industries.

14. An ester compound of the general formula (I):

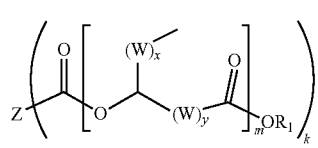

in which
- the radical Z is selected from the group including itaconic acid and diglycolic acid,
- the radical $R_1$ is selected from the group consisting of branched or unbranched C1- to C30-alkyl radicals, branched or unbranched C1- to C30-alkenyl radicals, C7- to C30-arylalkyl radicals, and C1- to C30-heteroarylalkyl radicals and C4- to C30-aryl radicals,
- the radical W is selected from the group consisting of —$CH_2$- and —CH=CH—,
- x is an integer from 1 to 20,
- y is an integer from 1 to 20,
- m is an integer from 1 to 10,
- k is an integer from 2 to 10.

15. An ester compound having the general formula (II)

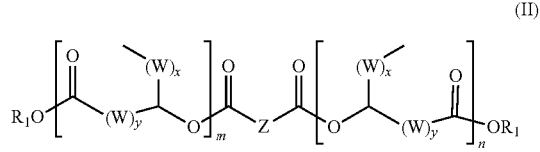

in which
- the radical Z is selected from the group including itaconic acid and diglycolic acid,
- the radical $R_1$ is selected from the group consisting of branched or unbranched $C_1$- to $C_{30}$-alkyl alkyl radicals, branched or unbranched $C_1$- to $C_{30}$-alkenyl radicals, $C_7$- to $C_{30}$-arylalkyl radicals and $C_1$- to $C_{30}$-heteroarylalkyl radicals and $C_4$- to $C_{30}$-aryl radicals,
- the radical W is selected from the group consisting of —$CH_2$- and —CH=CH—,
- x is an integer from 1 to 20,
- y is an integer from 1 to 20,
- m is an integer from 1 to 10,
- n is an integer from 1 to 10.

* * * * *